United States Patent [19]

Sugihara et al.

[11] Patent Number: 4,834,854
[45] Date of Patent: May 30, 1989

[54] METHOD OF MAKING AN ELECTROPHORESIS MEDIUM

[75] Inventors: Mitsuru Sugihara, Saitama; Mineo Suyefuji, Kanagawa, both of Japan

[73] Assignee: Fuji Photo Film Co., Ltd., Kanagawa, Japan

[21] Appl. No.: 234,470

[22] Filed: Aug. 19, 1988

[30] Foreign Application Priority Data

Aug. 20, 1987 [JP] Japan ................................ 62-207257
Aug. 20, 1987 [JP] Japan ................................ 82-207258

[51] Int. Cl.$^4$ .............................................. G01N 27/26
[52] U.S. Cl. ................................ 204/182.8; 204/299 R; 204/180.1
[58] Field of Search .............. 204/182.8, 299 R, 180.1

[56] References Cited

U.S. PATENT DOCUMENTS 3,443,520  5/1969  Nejame, Jr. ..................... 366/161 X
4,620,794  11/1986  Leka ................................... 366/131
4,704,198  11/1987  Ebersole et al. ............. 204/182.8 X Primary Examiner—John F. Niebling
Assistant Examiner—John S. Starsick
Attorney, Agent, or Firm—Jules E. Goldberg

[57] ABSTRACT

A method of making an electrophoresis medium having a predetermined gradient in concentrations of an acrylamide compound and a cross-linking agent comprises the steps of mixing two kinds of aqueous solutions containing the acrylamide compound and the cross-linking agent in different concentrations such that a mixing ratio of the aqueous solutions to each other is changed gradually, thereby to form a predetermined gradual change (gradient) in concentrations of the acrylamide compound and the cross-linking agent in the mixture, and carrying out cross-linking polymerization of the mixture in the presence of a polymerization initiator. Viscosity values of the two kinds of the aqueous solutions containing the acrylamide compound and the cross-linking agent in different concentrations prior to the mixing are adjusted to be substantially equal to each other.

17 Claims, 2 Drawing Sheets

METHOD OF MAKING AN ELECTROPHORESIS MEDIUM

FIELD OF THE INVENTION

This invention relates to a method of making a membrane-shaped (layer-shaped) or pillar-shaped (prism-shaped or columnar) electrophoresis gel medium (hereinafter often referred to as a gel medium or a gel) containing an aqueous polyacrylamide gel for use in determination of base sequences in nucleic acids such as a DNA and a RNA or for use in separation and fractionation analysis of biopolymer constituents such as proteins or other polymeric substances.

BACKGROUND OF THE INVENTION

In the technique for determining base sequences in nucleic acids such as a DNA and a RNA according to the chemical degradation process, the dideoxy process or the like, slab electrophoresis using an electrophoresis medium membrane containing an aqueous polyacrylamide gel (hereinafter referred to as a polyacrylamide gel membrane or simply as a gel membrane) is indispensable. In recent years, electrophoresis analysis has come into wide use. Also, with the advances made in the dideoxy process, there has arisen a need for a polyacrylamide gel membrane capable of accurately separating up to a high molecular part of fragments of a nucleic acid.

On the other hand, in the case where fragments of a nucleic acid are electrophoretically separated based on a difference in its molecular weight for the base sequence determination of the nucleic acid and an ordinary polyacrylamide gel membrane is used for this purpose, the band intervals of the separated fragments become wider for a low molecular part and narrower for a high molecular part. As a result, the separation of the high molecular part of the nucleic acid fragments is deteriorated.

Also, an electrophoretic separation and fractionation technique has heretofore been widely utilized for the separation and fractionation analysis of constituents of a living organism. Particularly, the separation and fractionation analysis of proteins is frequently utilized in biochemical inspection for diagnosis of diseases. In the case where a protein is separated and fractionated by a single electrophoretic operation based on a difference in its molecular weight and an ordinary polyacrylamide gel membrane having constant concentration is used for this purpose, the band intervals of the separated and fractionated protein become wider for a low molecular part and narrower for a high molecular part. As a result, the separation of the high molecular part of the protein is deteriorated.

DESCRIPTION OF THE PRIOR ART

Accordingly, in order to achieve good separation performance uniformly over a wide molecular weight range from a low molecular part to a high molecular part, there has heretofore been used a polyacrylamide gel membrane (gradient gel membrane) having a gradient in the acrylamide concentration or a gradient in the buffer concentration along the direction of electrophoretic migration. For example, Japanese Unexamined Patent Publication No. 60(1985)-235819 (EP No. 0 159 694A, U.S. Pat. No. 4,704,198) discloses a process of and an apparatus for producing an electrophoresis medium membrane containing a polyacrylamide gel and having a gradient in the polyacrylamide concentration (gel concentration gradient or pore size gradient) by polymerizing and cross-linking a thin layer of an aqueous solution containing acrylamide and a cross-linking agent on a support surface by use of ionized radiation such as electron beams. The apparatus for carrying out the disclosed process and the method of controlling the electron beams or the like for forming the concentration gradient in the gel membrane are very complicated. Also, it was found that, in the case where a polyacrylamide gel membrane (concentration gradient gel membrane) imparted with a gel concentration gradient is made by casting or application in accordance with, for example, a method proposed in Japanese Patent Application No. 62(1987)-129924, the membrane thickness fluctuates and the electrophoretic image or the migration pattern is disturbed in the direction of casting or application as the concentration of the aqueous coating solution is changed.

SUMMARY OF THE INVENTION

The primary object of the present invention is to provide an improved method of making an electrophoresis medium containing an aqueous polyacrylamide gel for use in determination of base sequences in nucleic acids such as a DNA and a RNA and having a concentration gradient of the aqueous polyacrylamide gel, which electrophoresis medium has substantially uniform, high separation effects over a wide molecular weight range from a low molecular part to a high molecular part of fragments of a nucleic acid, and exhibits no or little disturbance of an electrophoretic image or a migration pattern.

Another object of the present invention is to provide an improved method of making a membrane-shaped (layer-shaped) electrophoresis medium (hereinafter referred to as a gel medium membrane or a gel membrane) containing an aqueous polyacrylamide gel for use in determination of base sequences in nucleic acids such as a DNA and a RNA and having a concentration gradient of the aqueous polyacrylamide gel, which electrophoresis medium is free of or almost free of irregular or uncontrollable fluctuation in the membrane thickness accompanying a gradual change (gradient) in the concentration of the aqueous polyacrylamide gel.

A further object of the present invention is to provide an improved method of making a membrane-shaped or pillar shaped (prism-shaped or columnar) electrophoresis medium having a concentration gradient of an aqueous polyacrylamide gel, which electrophoresis medium has substantially uniform, high separation effects over a wide molecular weight range from a low molecular part to a high molecular part of a biopolymer constituent such as a protein or other polymeric constituent, and exhibits no or little disturbance of an electrophoretic image or a migration pattern.

A still further object of the present invention is to provide an improved method of making a membrane-shaped (layer-shaped) electrophoresis medium (hereinafter referred to as a gel medium membrane or a gel membrane) containing an aqueous polyacrylamide gel for use in separation and fractionation analysis of biopolymer constituents such as proteins or other polymeric substances and having a concentration gradient of the aqueous polyacrylamide gel, which electrophoresis medium is free of or almost free of irregular or uncontrollable fluctuation in the membrane thickness accompanying a gradual change (gradient) in the concentration of the aqueous polyacrylamide gel.

The present invention provides a first method of making an electrophoresis medium having a predetermined gradient in concentrations of an acrylamide compound and a cross-linking agent (i.e. a concentration gradient of an aqueous polyacrylamide gel) and containing a compound having at least one carbamoyl group in its molecule as a denaturing agent (or modifier) by mixing two kinds of aqueous solutions containing the acrylamide compound and the cross-linking agent in different concentrations such that a mixing ratio of the aqueous solutions to each other is changed gradually, thereby to form a predetermined gradual change in concentrations of the acrylamide compound and the cross-linking agent in the mixture, and carrying out cross-linking polymerization of the mixture in the presence of a polymerization initiator, wherein the improvement comprises the step of adjusting so that viscosity values of the two kinds of said aqueous solutions containing the acrylamide compound and the cross-linking agent in different concentrations prior to said mixing are substantially equal to each other.

The present invention also provides a second method of making an electrophoresis medium having a predetermined gradient in concentrations of an acrylamide compound and a cross-linking agent (i.e. a concentration gradient of an aqueous polyacrylamide gel) by mixing two kinds of aqueous solutions containing the acrylamide compound and the cross-linking agent in different concentrations such that a mixing ratio of the aqueous solutions to each other is changed gradually, thereby to form a predetermined gradual change in concentrations of the acrylamide compound and the cross-linking agent in the mixture, and carrying out cross-linking polymerization of the mixture in the presence of a polymerization initiator, wherein the improvement comprises the step of adjusting so that viscosity values of the two kinds of said aqueous solutions containing the acrylamide compound and the cross-linking agent in different concentrations prior to said mixing are substantially equal to each other.

With the first method of making an electrophoresis medium in accordance with the present invention, it is possible to obtain an electrophoresis medium containing the aqueous polyacrylamide gel for use in determination of base sequences in nucleic acids such as a DNA and a RNA and having the concentration gradient of the aqueous polyacrylamide gel, which electrophoresis medium has substantially uniform, high separation effects over a wide molecular weight range from a low molecular part to a high molecular part of fragments of a nucleic acid, and exhibits no or little disturbance of an electrophoretic image or a migration pattern.

Also, with the first method of making an electrophoresis medium in accordance with the present invention, it is possible to obtain a gel medium membrane containing the aqueous polyacrylamide gel for use in determination of base sequences in nucleic acids such as a DNA and a RNA and having the concentration gradient of the aqueous polyacylamide gel, which gel medium membrane is free of or almost free of irregular or uncontrollable fluctuation in the membrane thickness accompanying the gradual change (gradient) in the concentration of the aqueous polyacrylamide gel.

With the second method of making an electrophoresis medium in accordance with the present invention, it is possible to obtain a membrane-shaped or pillar shaped (prism-shaped or columnar) electrophoresis medium having the concentration gradient of the aqueous polyacrylamide gel, which electrophoresis medium has substantially uniform, high separation effects over a wide molecular weight range from a low molecular part to a high molecular part of a biopolymer constituent such as a protein or other polymeric constituent, and exhibits no or little disturbance of an electrophoretic image or a migration pattern.

Also, with the second method of making an electrophoresis medium in accordance with the present invention, it is possible to obtain a gel medium membrane containing the aqueous polyacrylamide gel for use in separation and fractionation analysis of biopolymer constituents such as proteins or other polymeric substances and having a concentration gradient of the aqueous polyacrylamide gel, which gel medium membrane is free of or almost free of irregular or uncontrollable fluctuation in the membrane thickness accompanying a gradual change (gradient) in the concentration of the aqueous polyacrylamide gel.

The first and second methods of making an electrophoresis medium containing the aqueous polyacrylamide gel in accordance with the present invention are applicable nearly equally to a membrane-shaped (layer-shaped) gel medium and a pillar-shaped (prism-shaped or columnar) gel medium. Therefore, the first and second methods of making an electrophoresis medium in accordance with the present invention will hereinbelow be described mainly for the membrane-shaped (layer-shaped) gel medium (i.e. the gel medium membrane).

The acrylamide compound (monomer) for use in the preparation of the electrophoresis gel medium may be, for example, acrylamide or an acrylamide homologue such as N-methylacrylamide, N,N-dimethylacrylamide, N-(hydroxymethyl)acrylamide, or diacetone acrylamide. These compounds may be used alone, or two or more of these compounds may be used in combination. Among these compounds, acrylamide is preferable. A combination of acrylamide with one or more of the other acrylamide compounds is also preferable.

The cross-linking agent may be selected from bifunctional cross-linking agents disclosed in "Electrophoresis," 2(4), 213–219 (1981) and "Electrophoresis," 2(4), 220–228 (1981), and tri- or poly-functional cross-linking agents disclosed in Japanese Unexamined Patent Publication No. 61(1986)-2058. The bifunctional cross-linking agents include, for example, N,N'-methylenebisacrylamide (BIS), N,N'-propylenebisacrylamide (PBA), diacrylamide dimethyl ether (DAE), 1,2-diacrylamide ethylene glycol (DEG), ethyleneureabisacrylamide (EUB), ethylenediacrylate (EDA), N,N'-diallyltartardiamide (DATD), and N,N'-bisacrylylcystamine (BAC). The trifunctional cross-linking agents include, for example, 1,3,5-triacryloylhexahydro-s-triazine (TAHT), triallyl cyanurate (TAC), and triallyl isocyanurate (TAIC). Among these cross-linking agents, BIS and TAHT are preferable. Also, two or more cross-linking agents may be used in combination.

The cross-linking agent is used in a ratio within the range of approximately 0.5 wt % to approximately 30 wt % based on the total weight of the monomer and the cross-linking agent, preferably within the range of approximately 1.0 wt % to approximately 10 wt % based on the total weight of the monomer and the cross-linking agent.

In order to adjust the viscosity and for other purposes, the aqueous solutions for gel formation used for the formation of the gel medium may also be added with at least one kind of agarose and/or at least one kind of a water-soluble polymer such as a water-soluble cellulose derivative or a polyacrylamide.

The agarose may be selected from lowelectroendosmotic agarose, medium-electroendosmotic agarose, and high-electroendosmotic agarose as disclosed in, for example, Japanese Unexamined Patent Publication Nos. 55(1980)-5730, 55(1980)-110946, 57(1982)-502098 and 59(1984)-126236. The amount of agarose added may be within the range of approximately 0.1% w/v to approximately 2.0% w/v based on the volume of the aqueous gel containing the monomer and the cross-linking agent, preferably within the range of approximately 0.2% w/v to approximately 1.2% w/v based on the volume of the aqueous gel containing the monomer and the cross-linking agent.

The water-soluble polymer may be a water-soluble, nonionic addition or condensation polymer having a molecular weight within the range of approximately 10,000 to approximately 1,000,000 as disclosed in, for example, Japanese Unexamined Patent Publication No. 59(1984)-126236 or 60(1985)-60548, a cross-linkable acrylamide copolymer containing a vinylsulfonyl group or the like as disclosed in, for example, Japanese Unexamined Patent Publication No. 61(1986)-18852, or a water-soluble cellulose derivative as disclosed in, for example, Japanese Unexamined Patent Publication No. 63(1988)-70156. The water-soluble, nonionic addition polymer may be, for example, polyacrylamide, polyvinyl alcohol, or polyvinyl pyrrolidone. The water-soluble nonionic condensation polymer may be, for example, polyethylene glycol, polypropylene glycol, or poly-N-vinyl pyrrolidone. The cross-linkable acrylamide copolymer may be, for example, a N-[[3-(vinylsulfonyl)propaneamide]methyl]acrylamide-acrylamide copolymer, or a N-[[3-(2-chloroethylsulfonyl)-propaneamide]methyl]acrylamide-acrylamide-N-1,1-dimethyl-3-oxobutyl)acrylamide copolymer. The water-soluble cellulose derivative may be, for example, a water-soluble cellulose ether such as methyl cellulose, ethyl cellulose, hydroxyethyl cellulose, hydroxypropylmethyl cellulose or hydroxybutylmethyl cellulose. Among the above-enumerated water-soluble polymers, polyacrylamide, polyethylene glycol, and the N-[[3-(vinylsulfonyl)propaneamide]methyl]acrylamide-acrylamide copolymer are preferable. In the case where the water-soluble, nonionic addition or condensation polymer is employed as the water-soluble polymer, the amount thereof added may be within the range of appooximately 2 wt % to approximately 100 wt % based on the total weight of the monomer and the cross-linking agent, preferably within the range of approximately 5 wt % to approximately 50 wt % based on the total weight of the monomer and the cross-linking agent. In the case where the cross-linkable acrylamide copolymer is employed as the water-soluble polymer, the amount thereof added may be within the range of approximately 1 wt % to approximately 50 wt % based on the weight of the acrylamide compound, preferably within the range of approximately 5 wt % to approximately 40 wt % based on the weight of the acrylamide compound.

In order to prevent broadening of the band width in the electrophoretic image of the high molecular part of the nucleic acid fragments and distortion of the separation image, the gel medium may be added with grycerol in a ratio within the range of approximately 0.1% w/v to approximately 1.0% w/v based on the volume of the gel medium. Also, a polyol compound such as grycerol or ethylene glycol may be added as a wetting agent to the gel medium in a ratio within the range of approximately 1% w/v to approximately 40% w/v based on the volume of the gel medium.

The addition of agarose and/or the water-soluble polymer should preferably be carried out at the time between preparation of the aqueous solutions for gel formation and mixing of the two kinds of the aqueous solutions for gel formation having different concentrations. The addition of the polyol compound such as grycerol or ethylene glycol may be carried out at any time between dissolution of the monomer and the cross-linking agent into water and formation of the aqueous polyacrylamide gel (or loading into a tube), and should preferably be carried out at the time between dissolution of the monomer and the cross-linking agent into water and a step prior to mixing of the two kinds of the aqueous solutions for gel formation having different concentrations and casting or application of the mixture (or prior to loading into a tube).

In the first method of making an electrophoresis medium in accordance with the present invention, the gel medium may be added with a nonionic, anionic or amphoteric surface active agent. The nonionic surface active agent may be, for example, the compound having the formula of

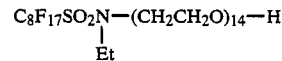

The anionic surface active agent may be, for example, the compound having the formula of

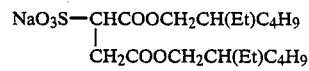

The amphoteric surface active agent may be, for example, the compound having the formula of

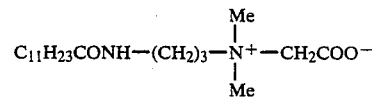

In the case where the nonionic or cationic surface active agent is used, the amount thereof added may be within the range of approximately $1\times10^{-4}$% w/v to approximately $5\times10^{-1}$% w/v based on the volume of the aqueous gel containing the monomer and the cross-linking agent, preferably within the range of approximately $1\times10^{-3}$% w/v to approximately $1\times10^{-2}$% w/v based on the volume of the aqueous gel containing the monomer and the cross-linking agent. In the case where the anionic surface active agent is used, the amount thereof added may be within the range of approximately $1\times10^{-4}$% w/v to approximately $5\times10^{-2}$% w/v based on the volume of the aqueous gel containing the monomer and the cross-linking agent, preferably within the range of approximately $1\times10^{-3}$% w/v to approximately $5\times10^{-2}$% w/v based on the volume of the aqueous gel containing the monomer and the cross-linking agent.

Also, in the first method of making an electrophoresis medium in accordance with the present invention, the compound having at least one carbamoyl group such as urea or formamide is used as the denaturing agent (or modifier). The amount of the denaturing agent added is within the range of approximately 40% w/v to approximately 60% w/v based on the volume of the aqueous gel containing the monomer and the cross-linking agent. In the case where urea is used as the denaturing agent, the amount thereof used may be within the range of approximately 6 mols (approximately 360 g) to the saturation amount (approximately 420 g) per 1,000 ml of the aqueous gel containing the monomer and the cross-linking agent, preferably within the range of approximately 7 mols to the saturation amount per 1,000 ml of the aqueous gel containing the monomer and the cross-linking agent. Since the amount of the denaturing agent added is comparatively large, the addition thereof should preferably be carried out at the time the ingredients containing the monomer and the cross-linking agent are dissolved into water.

Furthermore, in the first method of making an electrophoresis medium in accordance with the present invention, a known pH buffer agent may be contained in the gel medium for adjusting the pH value during the electrophoresis to a value within the range of 8.0 to 9.0. The pH buffer agent may be selected from those described in "Kagaku Benran Kiso-hen" (Chemical Handbook, Fundamentals Ed.), Nihon Kagaku Kai, Maruzen, Tokyo, 1966, pp. 1312–1320; R. M. C. Dawson et al., "Data for Biochemical Research," 2nd ed., Oxford at the Clarendon Press, 1969, pp. 476–508; "Biochemistry," 5, pp. 467–477, 1966; and "Analytical Biochemistry," 104, pp. 300–310, 1980. By way of example, the pH buffer agent may be an agent containing tris(hydroxymethyl)aminomethane (Tris); N,N-bis(2-hydroxyethyl)glycine (Bicine); 4-(2-hydroxyethyl)-1-piperazinepropanesulfonic acid (HEPPS), Na salt or K salt; β-hydroxy-4-(2-hydroxyethyl)-1-piperazinepropanesulfonic acid (HEPPSO), Na salt or K salt; 3-[[2-hydroxy-1,1-bis(hydroxymethyl)ethyl]amino]-1-propanesulfonic acid (TAPS), Na salt or K salt; 3-(cyclohexylamino)-1-propanesulonic acid (CAPS), Na salt or K salt; or an acid, an alkali or a salt may be combined, when necessary, with one of the above-enumerated compounds. An example of preferable buffer agents is Tris-boric acidEDTA.2Na salt (composition for pH 8.2–8.3).

On the other hand, in the second method of making an electrophoresis medium in accordance with the present invention, in the case where a gel medium for use in separation and fractionation analysis of a protein or a conjugated protein such as lipoprotein or glycoprotein is to be made, it is generally preferable or indispensable that an anionic surface active agent be added as a denaturing agent (or modifier) to the electrophoresis medium. The addition of the anionic surface active agent to the electrophoresis medium enables efficient separation and fractionation of the protein or the conjugated protein and measurement of the molecular weight thereof. In the case where a gel medium for use in separation of nucleic acid fragments is to be made, the anionic surface active agent need not be added.

In the second method of making an electrophoresis medium in accordance with the present invention, the anionic surface active agent as the denaturing agent (or modifier) may be, for example, an alkyl sulfate, and should preferably be an alkyl sulfate having a long-chain alkyl group having 10 or more carbon atoms. In general, the cation for the formation of the salt may be an alkali metal ion such as a sodium ion, a potassium ion or a lithium ion, among which the sodium ion is suitable. Among the alkyl sulfates, a dodecylsulfate (sodium salt, potassium salt, lithium salt or the like) is preferable, and sodium dodecylsulfate (SDS) is most preferable.

Also, in the second method of making an electrophoresis medium in accordance with the present invention, the amount of the anionic surface active agent added as the denaturing agent is not larger than approximately 2.0% w/v, and should preferably be within the range of approximately 0.1% w/v to approximately 1.5% w/v based on the volume of the aqueous gel containing the monomer and the cross-linking agent. The addition of the denaturing agent should preferably be carried out at the time between dissolution of the ingredients containing the monomer and the cross-linking agent into water and formation of the aqueous gel.

Furthermore, in the second method of making an electrophoresis medium in accordance with the present invention, the gel medium may be added with a non-ionic, anionic or amphoteric surface active agent, which is of the type different from the denaturing agent. By way of example, the surface active agents enumerated above for the first method of making an electrophoresis medium in accordance with the present invention may be used in the same amount as mentioned above.

Moreover, in the second method of making an electrophoresis medium in accordance with the present invention, the gel medium may be added with a pH buffer agent selected from known pH buffer agents capable of adjusting the pH value during the electrophoresis to a desired value within the range of 2.5 to 10.0, depending on the sample subjected to electrophoresis. In the case where the gel medium is to be used in separation of nucleic acid fragments, the gel medium may be added with a pH buffer agent selected from known pH buffer agents capable of adjusting the pH value during the electrophoresis to a desired value within the range of 8.0 to 10.0, preferably within the range of 8.0 to 9.0. The pH buffer agent may be selected from those described in the references cited above for the pH buffer agents.

By way of example, the pH buffer agent used for adjusting the pH value to a value within the range of 2.5 to 10.0 in the second method of making an electrophoresis medium in accordance with the present invention, may be an agent containing barbital; an agent containing Tris; an agent containing a phosphate; an agent containing a borate; an agent containing acetic acid or an acetate; an agent containing citric acid or a citrate; an agent containing lactic acid or a lactate; an agent containing glycine; Bicine; HEPPS, Na salt or K salt; HEPPSO, Na salt or K salt; TAPS, Na salt or K salt; CAPS, Na salt or K salt; or an acid, an alkali or a salt which may be combined, when necessary, with one of the above-enumerated compounds. Examples of preferable buffer agents are potassium dihydrogenphosphate-disodium hydrogenphosphate, Tris-hydrochloric acid, Tris-sodium borate, Tris-sodium borate-EDTA.2Na salt, Tris-citric acid, sodium barbital-sodium acetate, sodium barbital-hydrochloric acid, barbital-sodium barbital, acetic acid-sodium acetate, lactic acid-sodium lactate, citric acid-sodium dihydrogenphosphate, Bicine, HEPPS, HEPPS.Na salt, HEPPSO, HEPPSO.Na salt, TAPS, TAPS.Na salt, CAPS, and CAPS.Na salt.

By way of example, the pH buffer agent used for adjusting the pH value to a value within the range of 8.0 to 10.0 in the second method of making an electrophoresis medium in accordance with the present invention, may be Tris; Bicine; HEPPS, Na salt or K salt; HEPPSO, Na salt or K salt; TAPS, Na salt or K salt; CAPS, Na salt or K salt; or an acid, an alkali or a salt which may be combined, when necessary, with one of the above-enumerated compounds. Examples of preferable buffer agents are Tris-boric acid-EDTA.2Na salt (composition for pH8.2-8.3), Tris-hydrochloric acid (composition for pH8.9), CAPS.Na salt (composition for pH8.9), and Tris-glycine.

In general, in the first and second methods of making an electrophoresis medium in accordance with the present invention, the gel medium membrane having a predetermined thickness should preferably be substantially colorless and transparent for the detection or reading of the electrophoretic image or the migration pattern.

The gel medium membrane is provided as a membrane or a layer having a predetermined thickness on a substantially electrically non-conductive, water-impermeable, planar sheet-shaped (film-shaped or plate-shaped) support or cover sheet having a flat, smooth surface. A known glass plate, an organic polymer sheet, or the like may be used as the substantially electrically non-conductive, water-impermeable, planar support or cover sheet having a smooth surface. The organic polymer sheet may be formed of, for example, polyethylene terephthalate, bisphenol A polycarbonate, polystyrene, or a polymer of cellulose ester (for example, cellulose diacetate, cellulose triacetate or cellulose acetate propionate). The organic polymer sheet may be a planar sheet-shaped material or a plate-shaped material having a smooth surface and a thickness within the range of approximately 50 μm to approximately 2 mm, preferably within the range of approximately 80 μm to approximately 500 μm, and transparent, i.e. permeable to at least a part of electromagnetic radiations having a wavelength within the range of approximately 200 nm to approximately 900 nm. In the case where the organic polymer support or the cover sheet is used, in order to make the surface hydrophilic and to improve adhesion to the gel membrane, the organic polymer support or the cover sheet may be subjected to known surface processing such as irradiation of ultraviolet rays, glow discharge processing, corona discharge processing, flame treatment, irradiation of electron beams, chemical etching or electrolytic etching. On the surface of the organic polymer support or the cover sheet, a subbing layer or an adhesive layer as disclosed in, for example, Japanese Unexamined Patent Publication Nos. 59(1984)-164950, 59(1984)-212753, 60(1985)-194349, 60(1985)-239658, 60(1985)-244850 and 61(1986)-14557 may be provided when necessary to strengthen the adhesion of the support or the cover sheet to the gel medium layer.

In order to gradually and continuously change the mixing ratio of the two kinds of the solutions for gel formation having different concentrations, it is possible to employ various known methods. For example, it is possible to employ a method as described in "Tanpakushitsu.Koso No Kisojikkenho" (Basic Experimental Method for Proteins and Enzymes), Horio and Yamashita, Nankodo, 1981, pp. 304-308, and Japanese Unexamined Patent Publication No. 54(1979)-43881, wherein a vessel containing an aqueous solution for gel formation which contains a monomer (acrylamide compound), a cross-linking agent and a polymerization initiator in relatively high concentrations and a vessel containing an aqueous solution for gel formation which contains the monomer (acrylamide compound), the crosslinking agent and the polymerization initiator in relatively low concentrations are connected with each other by a conduit at positions slightly above the bottom surfaces of the vessels, a solution mixture feed-out conduit is connected to one of the vessels at a position slightly above the bottom surface of the vessel, the solution in the vessel to which the solution mixture feed-out conduit is connected (the vessel containing the high-concentration aqueous solution or the vessel containing the low-concentration aqueous solution) is stirred, and the solution mixture is fed out by a pump provided at an intermediate point of the solution mixture feed-out conduit. It is also possible to employ a method as disclosed in Japanese Unexamined Patent Publication No. 62(1987)-167459 using an apparatus provided with two aqueous solution accommodating vessels containing a high-concentration aqueous solution for gel formation and a low-concentration aqueous solution for gel formation respectively, a single mixing and stirring vessel for receiving, mixing and stirring the two kinds of the aqueous solutions for gel formation, solution feed conduits for feeding the aqueous solutions for gel formation from the two aqueous solution accommodating vessels to the mixing and stirring vessel, solution feed flow rate adjusting means provided at intermediate points of the respective solution feed conduits, a control means for controlling the respective solution feed flow rate adjusting means to adjust the solution feed flow rates in accordance with signals (information) corresponding to gradual change functions of predetermined flow rate, and a casting or application means connected with a leading edge of a single solution feed conduit coming from the mixing and stirring vessel. It is also possible to employ a method as proposed in Japanese Patent Application No. 62(1987)-129924 wherein a high-concentration aqueous solution for gel formation and a low-concentration aqueous solution for gel formation are fed out by solution feed-out means (pumps) in a flow rate ratio in accordance with a function corresponding to a predetermined gradual change, and are mixed with each other in a static mixer.

Adjustment of the viscosity values of the aqueous solutions for gel formation should preferably be carried out by adding at least one kind of agarose and/or at least one kind of a water-soluble polymer such as a water-soluble cellulose derivative or a polyacrylamide to the aqueous solutions for gel formation in such amounts that desired viscosity values are obtained. By this method, the viscosity values of the aqueous solutions for gel formation can be adjusted unsubstantially at desired values over a wide range of the content of the acrylamide compound.

The viscosity values of the high-concentration and low-concentration aqueous solutions for gel formation is within the range of approximately 1 cP to approximately 50 cP, preferably within the range of approximately 2 cP to approximately 20 cP, at a temperature within the range of approximately 0° C. to approximately 80° C., generally within the range of approximately 5° C. to approximately 50° C. By the term "viscosity values of two kinds of aqueous solutions for gel formation being substantially equal to each other (or substantially coincident with each other)" as used herein means that the difference between viscosity values of two kinds of aqueous solutions for gel formation is within the range of approximately 12%, preferably within the range of approximately 10%, above and below the mean (arithmetic mean) value of the viscosity values of two kinds of aqueous solutions for gel formation which are to be mixed with each other. The viscosity values of the aqueous solutions for gel formation may be measured by any method using a known viscometer such as a capillary viscometer, a falling ball viscometer, or a rotational viscometer. The temperatures of the aqueous solutions for gel formation at the time of viscosity measurement are within the range of approximately 0° C. to approximately 80° C., generally within the range of approximately 5° C. to approximately 50° C., and are substantially equal to the temperatures at the region of mixing of the two kinds of the aqueous solutions for gel formation and/or at the gel formation region.

The gel medium membrane is prepared by casting or applying the aqueous solution for gel formation obtained by mixing the aforesaid high-concentration and lowconcentration aqueous solutions for gel formation with each other and having a predetermined gradual change (gradient) in concentrations (i.e. the contents of the acrylamide compound and the cross-linking agent) in the membrane or layer form onto the planar support or the planar cover sheet, and polymerizing and cross-linking the monomer (acrylamide compound) with the cross-linking agent in the absence of molecular oxygen, when necessary with irradiation of ultraviolet rays or visible light or with heating, thereby forming a membrane or a layer of the aqueous polyacrylamide gel medium.

The prism-shaped or columnar gel medium is prepared by loading the aqueous solution for gel formation obtained by mixing the aforesaid two inds of the aqueous solutions for gel formation with each other and having the predetermined gradual change (gradient) in concentrations into a glass tube or an organic polymer tube which is substantially electrically non-conductive and water-impermeable and which has a smooth inner surface, and polymerizing and cross-linking the monomer (acrylamide compound) with the cross-linking agent in the absence of molecular oxygen, when necessary with irradiation of ultraviolet rays or visible light or with heating, thereby forming the aqueous polyacrylamide gel medium.

The acrylamide compound (monomer) and the cross-linking agent are dissolved or dispersed in water, and subjected to cross-linking polymerization in water to form the polymerized and cross-linked aqueous gel medium. In this specification, both dissolution (in water) and dispersion (in water) are generically referred to as dissolution (in water), and both the aqueous solution and the aqueous dispersion are generically referred to as the aqueous solution. Not only water but also a water-organic solvent mixture containing an organic solvent which may be added optionally may be used as the solvent or the dispersion medium.

A radical polymerization initiator composition used in accordance with the present invention may be selected from low-temperature radical polymerization initiator compositions described in "Electrophoresis," 2(4), 213–219 (1981), "Electrophoresis," 2(4), 220–228 (1981), Japanese Unexamined Patent Publication No. 59(1984)-126236, and "Saishin Denkieidoho" (Up-to-date Electrophoresis) by Aoki and Nagai (1973). The radical polymerization initiator composition may be, for example, a β-(dimethylamino)propionitrile (DMDPN)-ammonium peroxodisulfate mixture, a N,N,N',N'-tetramethylethylenediamine (TEMED)-ammonium peroxodisulfate mixture, a TEMED-riboflavin mixture, a TEMED-riboflavin-hydrogen peroxide mixture, a riboflavin-ammonium peroxodisulfate mixture, or a riboflavin-hydrogen peroxide mixture. (In the case where the photosensitizer such as riboflavin is used in combination, irradiation of ultraviolet rays or visible light is used in combination.) The amount of the radical polymerization initiator composition added is within the range of approximately 0.3 wt % to approximately 5.0 wt % based on the total weight of the monomer and the cross-linking agent, preferably within the range of approximately 0.5 wt % to approximately 3.0 wt % based on the total weight of the monomer and the cross-linking agent.

The gel concentration is adjusted such that the total weight of the monomer and the cross-linking agent is within the range of approximately 3% w/v to approximately 30% w/v based on the volume of the gel medium consisting of the monomer, the cross-linking agent and water, as expressed in accordance with the definition described in S. Hjerten, "Archives of Biochemistry and Biophysics," 1(Suppl.), 147–151 (1962).

In the course of the cross-linking polymerization of the solution for gel formation on the surface of the support (or the cover sheet), the casting or application of the solution for gel formation and the cross-linking polymerization should preferably be carried out in the absence of molecular oxygen, for example, in a nitrogen gas atmosphere, or the cross-linking polymerization should preferably be carried out by covering the surface of the cast or applied solution for gel formation by a covering material such as a cover film, a cover sheet or a cover plate exactly after the casting or application of the solution for gel formation. The covering material used for this purpose may be formed of the same material as the aforesaid support. In the case where an organic polymer film is used as the cover film, the thickness thereof may be approximately 300 μm or less, practically within the range of approximately 4 μm to approximately 200 μm, preferably within the range of approximately 4μm to approximately 100μm. In the case where a glass plate is used as the covering material, the thickness thereof may be nearly equal to the thickness of the planar glass plate used as the support. Also, the shape of the sample pouring portion may be selected from known shapes such as a rectangle, a square, a triangle (shark's teeth shape), and a circle.

The thickness of the gel medium membrane is generally within the range of approximately 50 μm to approximately 5 mm, preferably within the range of approximately 80 μm to approximately 1 mm. In the case where the gel medium membrane made by the second method of making an electrophoresis medium in accordance with the present invention is used for separation of nucleic acid fragments the thickness of the gel medium membrane should preferably be within the range of approximately 300 μm to approximately 3 mm.

The diameter of the columnar gel medium is generally within the range of approximately 3 mm to approximately 30 mm, preferably within the range of approximately 5 mm to approximately 20 mm.

The gel medium membrane or the pillar-shaped gel medium made by the methods in accordance with the present invention can be used for horizontal and vertical slab electrophoresis, column electrophoresis, disk electrophoresis and the like in accordance with the known processes described in the above-mentioned references.

DESCRIPTION OF THE PREFERRED EMBODIMENTS

The present invention will hereinbelow be described in further detail with reference to the following examples and the accompanying drawings.

EXAMPLE 1 AND COMPARATIVE EXAMPLE 1

A 10 mm-wide spacer plate having a constant thickness of 200 $\mu$m was secured by adhesion to both edges at longer sides of a colorless, transparent polyethylene terephthalate (PET) film as a planar support having a width of 20 cm and a thickness of 180 $\mu$m and having a smooth surface made hydrophilic by irradiation of ultraviolet rays.

On the other hand, two kinds of aqueous solutions for gel formation having the compositions indicated in column A in Table 1 below, having viscosity values nearly equal to each other (the difference between the viscosity values was 3.2% with respect to the arithmetic mean value of the viscosity values of the two kinds of the aqueous solutions for gel formation), and having different concentrations (i.e. different contents of the acrylamide compound and the cross-linking agent) were prepared.

Figure 1:
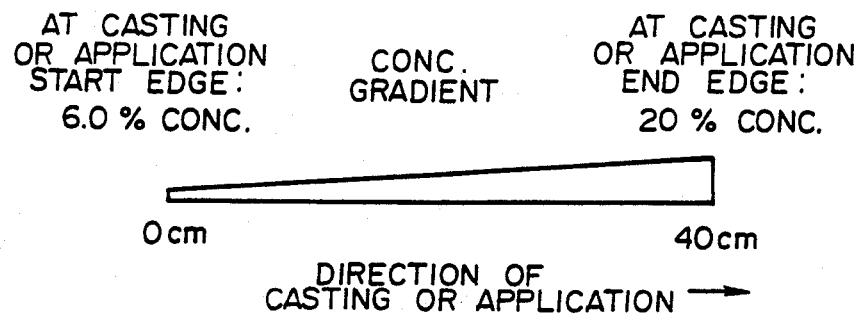
FIG. 1 is an explanatory sectional view showing a gradual change in gel concentration (concentration gradient) of aqueous polyacrylamide gel membranes having the gel concentration gradient in Example 1 in accordance with the present invention and Comparative Example 1 along the direction of casting or application (i.e. along the direction of electrophoretic migration)

The two kinds of the aqueous solutions for gel formation (without a polymerization initiator composition added thereto) were mixed by use of a static mixer in accordance with the method proposed in Japanese Patent Application No. 62(1987)-129924 by gradually changing the flow rate ratio (i.e. by initially adjusting the ratio of the low-concentration aqueous solution for gel formation to be high and then gradually increasing the ratio of the high-concentration aqueous solution for gel formation) so that a linear concentration gradient from a gel concentration of 6.0% to a gel concentration of 20% was obtained over a length of 40 cm in the direction of casting or application shown in FIG. 1, and by adding the polymerization initiator. The aqueous solution mixture thus obtained was fed at a constant flow rate to a casting or applying head. The aqueous solution mixture was cast at a constant flow rate onto the PET support in a nitrogen gas atmosphere, and the membrane of the aqueous solution mixture thus formed was subjected to cross-linking polymerization by irradiation from a 500 W xenon luminescent lamp in a nitrogen gas atmosphere. Then, a colorless, transparent PET sheet having a thickness of 63 $\mu$m and a width of 20 cm as a cover sheet was overlaid in close contact with the thus formed gel membrane. In this manner, an aqueous polyacrylamide gel membrane (1) (Example 1 using the first method of making an electrophoresis medium in accordance with the present invention) having a constant membrane thickness of 200 $\mu$m and having a change in gel concentration (concentration gradient) as shown in FIG. 1 was prepared.

On the other hand, an aqueous polyacrylamide gel membrane (2) (Comparative Example 1) having a constant membrane thickness of 200 $\mu$m and having the change in gel concentration (concentration gradient) as shown in FIG. 1 was prepared in the same manner as in Example 1, except that two kinds of aqueous solutions for gel formation having the compositions indicated in column B in Table 1 below, and having viscosity values unequal to each other (the difference between the viscosity values was 29.8% with respect to the arithmetic mean value of the viscosity values of the two kinds of the aqueous solutions for gel formation) were used.

Concentration gradients of gel membranes (1) and (2) (FIG. 1):

The gel concentration was increased almost linearly from the minimum of approximately 6.0% at the casting or application start edge to the maximum of approximately 20% at the casting or application end edge.

TABLE 1

Compositions of Aqueous Solutions for Gel Formation

| Ingredient | A (Example 1) Low | A (Example 1) High | B (Comp. Ex. 1) Low | B (Comp. Ex. 1) High |
|---|---|---|---|---|
| Acrylamide | 54.9 g | 183.0 g | 54.9 g | 183.0 g |
| 1,3,5-Triacryloyl-hexahydro-s-triazine | 570 mg | 1900 mg | 570 mg | 1900 mg |
| N—[[3-(vinylsulfonyl)propaneamide]methyl] acrylamide - acrylamide copolymer | 4.5 g | 15.0 g | 4.5 g | 15.0 g |
| Agarose | 6.5 g | 4.0 g | 4.5 g | 4.5 g |
| Polyvinyl pyrrolidone (average molecular weight: 40,000) | 2.9 g | ← | ← | ← |
| Urea | 420 g | ← | ← | ← |
| [pH buffer agent] | | | | |
| Tris | 12.1 g | ← | ← | ← |
| Boric acid | 6.5 g | ← | ← | ← |
| EDTA·2Na | 750 mg | ← | ← | ← |
| Water added to make up to | 1,000 ml | ← | ← | ← |
| [Polymerization initiator] | | | | |
| Ammonium peroxodisulfate (5.0 wt % aqueous solution) | 13 ml | ← | ← | ← |
| [Polymerization initiator] | | | | |
| N,N,N',N'—tetramethyl-ethylenediamine (25 wt % aqueous solution) | 330 μl | ← | ← | ← |
| Na riboflavin phosphate ester (0.25 wt % aqueous solution) | 15 ml | ← | ← | ← |
| Measured viscosity values (at 15° C.) | 10.7 cP | 11.4 cP | 8.0 cP | 14.8 cP |

←: Indicates the same value and the same unit as in the left column.
Agarose: Low electroendosmotic, gelling temperature 36° C.
Measured viscosity value: Measured at 15° C. with a rotational viscometer.
Low, High: Indicates low-concentration and high-concentration aqueous solutions for gel formation respectively.

Figure 2:
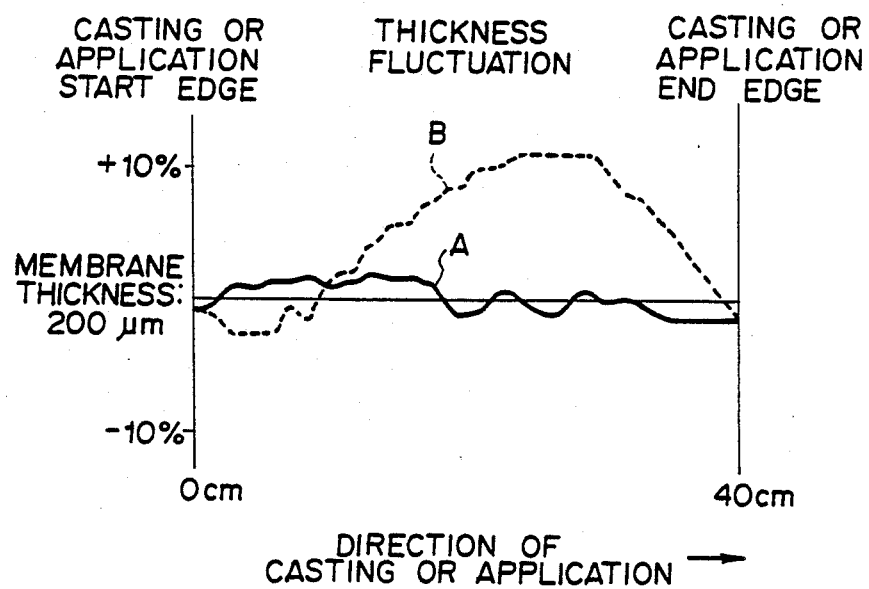
FIG. 2 is an explanatory graph showing measured values of fluctuations in the thicknesses of aqueous polyacrylamide gel membranes having the gel concentration gradient in Example 1 in accordance with the present invention and Comparative Example 1 along the direction of casting or application, in terms of fluctuation percentage with respect to a predetermined membrane thickness (200 $\mu$m), wherein A denotes a fluctuation percentage curve of a gel membrane (1) made by the first method of making an electrophoresis medium in accordance with the present invention, and B denotes a fluctuation percentage curve of a gel membrane (2) made in Comparative Example (1) by use of the conventional technique.

The membrane thicknesses of the two types of the gel membranes were measured. As a result, it was found that, in the case of the gel membrane (1) having the concentration gradient and the constant membrane thickness prepared by mixing the two kinds of the aqueous solutions for gel formation having equal viscosity values by the first method of making an electrophoresis medium in accordance with the present invention, as indicated by A in FIG. 2, fluctuations of the membrane thickness as the gel concentration was increased were within the range of from the minimum of approximately −1.6% to the maximum of approximately +2.0% with respect to the predetermined membrane thickness, and thus the thickness uniformity was high. On the other hand, in the case of the gel membrane (2) prepared by mixing the two kinds of the aqueous solutions for gel formation having unequal viscosity values in Comparative Example 1, as indicated by B in FIG. 2, fluctuations of the membrane thickness as the gel concentration was increased were within the range of from the minimum of approximately 2.5% to the maximum of approximately 11.0% with respect to the predetermined membrane thickness, and the membrane thickness partially increased as the gel concentration was increased. Thus, the thickness uniformity of the gel membrane (2) was low. Specifically, the fluctuation range of the membrane thickness of the gel membrane made by the first method of making an electrophoresis medium in accordance with the present invention was approximately one fourth of the fluctuation range of the membrane thickness of the gel membrane made in Comparative Example 1 using the conventional technique.

Performance evaluation test:

The aforesaid two types of the gel membranes were provided with a sample spotting portion, and electrophoretic separation of a DNA fragment for the base sequence determination of a DNA and formation of autoradiographic images were carried out in accordance with the conventional method by using the two types of the gel membranes and DNA fragment samples prepared by the dideoxy process for M13mp8DNA.

As a result, it was found that, with the gel membrane (1) having the gel concentration gradient made by the first method of making an electrophoresis medium in accordance with the present invention, the electrophoresis lanes were in the straight line form and thus were normal, and no disturbance arose in the DNA fragment separation pattern, though slight smiling arose. On the other hand, with the gel membrane (2) having the gel concentration gradient made in Comparative Example 1 using the conventional technique, the electrophoresis lanes were in a curved form having large W-shaped undulation, and disturbance arose in the DNA fragment separation pattern.

The aforesaid results revealed that the electrophoresis medium membrane containing the aqueous polyacrylamide gel and having the concentration gradient and the constant membrane thickness prepared by the first method of making an electrophoresis medium in accordance with the present invention, wherein the two kinds of the aqueous solutions for gel formation having substantially equal viscosity values and different concentrations are mixed with each other, is of a high quality having a very constant membrane thickness and normal, straight-line DNA electrophoresis lanes, and free of disturbance of DNA fragment separation patterns.

EXAMPLE 2 AND COMPARATIVE EXAMPLE 2

A 10mm-wide spacer plate having a constant thickness of 800 μm was secured by adhesion to both edges at longer sides of a colorless, transparent polyethylene terephthalate (PET) film as a planar support having a width of 20 cm and a thickness of 180 μm and having a smooth surface made hydrophilic by irradiation of ultraviolet rays.

On the other hand, two kinds of aqueous solutions for gel formation having the compositions indicated in column C in Table 2 below, having viscosity values nearly equal to each other (the difference between the viscosity values was 1.8% with respect to the arithmetic mean value of the viscosity values of the two kinds of the aqueous solutions for gel formation), and having different concentrations (i.e. different contents of the acrylamide compound and the cross-linking agent) were prepared.

Figure 3:
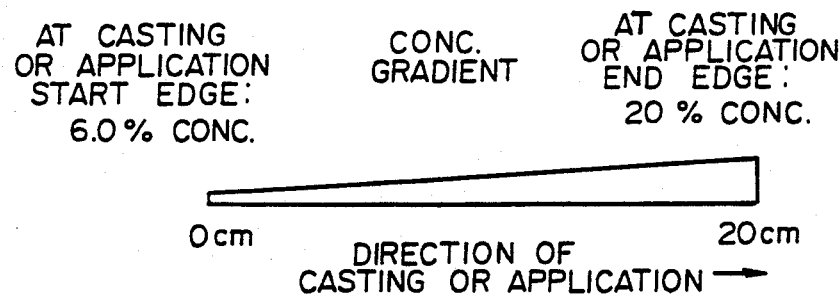
FIG. 3 is an explanatory sectional view showing a gradual change in gel concentration (concentration gradient) of aqueous polyacrylamide gel membranes having the gel concentration gradient in Example 2 in accordance with the present invention and Comparative Example 2 along the direction of casting or application (i.e. along the direction of electrophoretic migration)

The two kinds of the aqueous solutions for gel formation (without a polymerization initiator composition added thereto) were mixed by use of a static mixer in accordance with the method proposed in Japanese Patent Application No. 62(1987)-129924 by gradually changing the flow rate ratio (i.e. by initially adjusting the ratio of the low-concentration aqueous solution for gel formation to be high and then gradually increasing the ratio of the high-concentration aqueous solution for gel formation) so that a linear concentration gradient from a gel concentration of 6.0% to a gel concentration of 20% was obtained over a length of 20 cm in the direction of casting or application shown in FIG. 3, and by adding the polymerization initiator. The aqueous solution mixture thus obtained was fed at a constant flow rate to a casting or applying head. The aqueous solution mixture was cast at a constant flow rate onto the PET support in a nitrogen gas atmosphere, and the membrane of the aqueous solution mixture thus formed was subjected to cross-linking polymerization by irradiation from a 500 W xenon luminescent lamp in a nitrogen gas atmosphere. Then, a colorless, transparent PET sheet having a thickness of 63 μm and a width of 20 cm as a cover sheet was overlaid in close contact with the thus formed gel membrane. In this manner, an aqueous polyacrylamide gel membrane (3) (Example 2 using the second method of making an electrophoresis medium in accordance with the present invention) having a constant membrane thickness of 800 μm and having a change in gel concentration (concentration gradient) as shown in FIG. 3 was prepared.

On the other hand, an aqueous polyacrylamide gel membrane (4) (Comparative Example 2) having a constant membrane thickness of 800 μm and having the change in gel concentration (concentration gradient) as shown in FIG. 3 was prepared in the same manner as in Example 2, except that two kinds of aqueous solutions for gel formation having the compositions indicated in column D in Table 2 below, and having viscosity values unequal to each other (the difference between the viscosity values was 20.7% with respect to the arithmetic mean value of the viscosity values of the two kinds of the aqueous solutions for gel formation) were used.

Concentration gradients of gel membranes (3) and (4) (FIG. 3):

The gel concentration was increased almost linearly from the minimum of approximately 6.0% at the casting or application start edge to the maximum of approximately 20% at the casting or application end edge.

TABLE 2

| | Compositions of Aqueous Solutions for Gel Formation | | | |
| | C (Example 2) | | D (Comp. Ex. 2) | |
| Ingredient | Low | High | Low | High |
| --- | --- | --- | --- | --- |
| Acrylamide | 54.9 g | 183.0 g | 54.9 g | 183.0 g |
| 1,3,5-Triacryloyl-hexahydro-s-triazine | 570 mg | 1,900 mg | 570 mg | 1,900 mg |
| N—[[3-(vinylsulfonyl)propaneamide]methyl] acrylamide - acrylamide copolymer | 4.5 g | 15.0 g | 4.5 g | 15.0 g |
| Polyacrylamide (average molecular weight: 700,000) | 20.0 g | 16.0 g | None | None |
| Sodium dodecylsulfate [pH buffer agent] | 1,000 mg | ← | ← | ← |
| 1.5M-Tris-hydrochloric acid (pH 8.8) | 250 ml | ← | ← | ← |
| Water added to make up to [Polymerization initiator] | 1,000 ml | ← | ← | ← |
| Ammonium peroxodisulfate (2.5 wt % aqueous solution) | 24 ml | ← | ← | ← |
| N,N,N',N'—tetramethyl-ethylenediamine (25 wt % aqueous solution) [Polymerization initiator] | 250 μl | ← | ← | ← |
| Na riboflavin phosphate ester (0.25 wt % aqueous solution) | 20 ml | ← | ← | ← |
| Measured viscosity | 13.7 cP | 14.2 cP | 2.1 cP | 3.2 cP |

TABLE 2-continued

| | Compositions of Aqueous Solutions for Gel Formation | | | |
|---|---|---|---|---|
| | C (Example 2) | | D (Comp. Ex. 2) | |
| Ingredient | Low | High | Low | High |
| values (at 15° C.) | | | | |

←: Indicates the same value and the same unit as in the left column.
Measured viscosity value: Measured at 15° C. with a rotational viscometer.
Low, High: Indicates low-concentration and high-concentration aqueous solutions for gel formation respectively.

Figure 4:
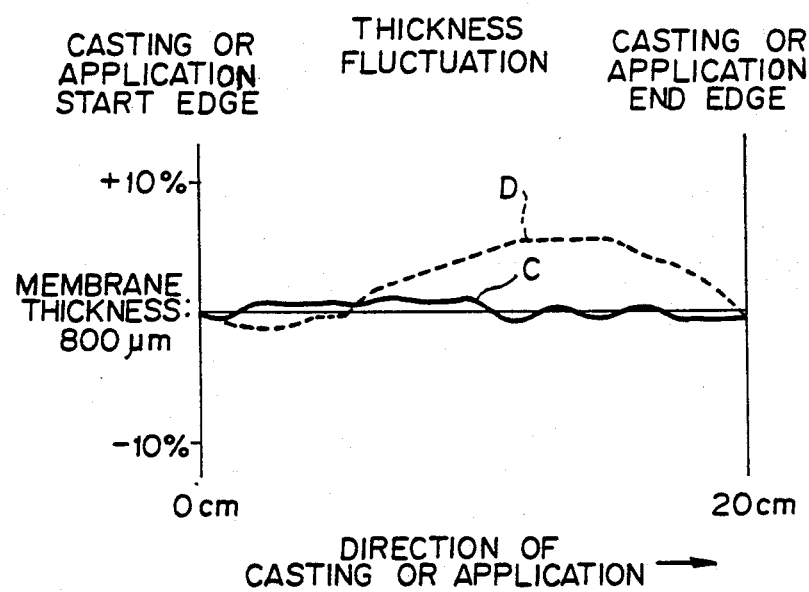
FIG. 4 is an explanatory graph showing measured values of fluctuations in the thicknesses of aqueous polyacrylamide gel membranes having the gel concentration gradient in Example 2 in accordance with the present invention and Comparative Example 2 along the direction of casting or application, in terms of fluctuation percentage with respect to a predetermined membrane thickness (800 $\mu$m), wherein C denotes a fluctuation percentage curve of a gel membrane (3) made by the second method of making an electrophoresis medium in accordance with the present invention, and D denotes a fluctuation percentage curve of a gel membrane (4) made in Comparative Example (2) by use of the conventional technique.

The membrane thicknesses of the two types of the gel membranes were measured. As a result, it was found that, in the case of the gel membrane (3) having the concentration gradient and the constant membrane thickness prepared by mixing the two kinds of the aqueous solutions for gel formation having equal viscosity values by the second method of making an electrophoresis medium in accordance with the present invention, as indicated by C in FIG. 4, fluctuations of the membrane thickness as the gel concentration was increased were within the range of from the minimum of approximately −0.8% to the maximum of approximately +1.0% with respect to the predetermined membrane thickness, and thus the thickness uniformity was high. On the other hand, in the case of the gel membrane (4) prepared by mixing the two kinds of the aqueous solutions for gel formation having unequal viscosity values in Comparative Example 2, as indicated by D in FIG. 4, fluctuations of the membrane thickness as the gel concentration was increased were within the range of from the minimum of approximately −1.3% to the maximum of approximately +5.5% with respect to the predetermined membrane thickness, and the membrane thickness partially increased as the gel concentration was increased. Thus, the thickness uniformity of the gel membrane (4) was low. Specifically, the fluctuation range of the membrane thickness of the gel membrane made by the second method of making an electrophoresis medium in accordance with the present invention was approximately one fourth of the fluctuation range of the membrane thickness of the gel membrane made in Comparative Example 2 using the conventional technique.

Performance evaluation test:

The aforesaid two types of the gel membranes were provided with a sample spotting portion. Electrophoretic separation and fractionation were carried out in accordance with the conventional method by using the two types of the gel membranes and reference proteins listed below.

α-Lactalbumin (molecular weight: 14,400)
Soybean trypsin inhibitor (molecular weight: 20,100)
Carbonic anhydrase (molecular weight: 30,000)
Ovalbumin (molecular weight: 43,000)
Bovine albumin (molecular weight: 67,000)
Phosphorylase b (molecular weight: 94,000)

The electrophoretic images were dyed with Coomassie Blue R-250.

As a result, it was found that, with the gel membrane (3) having the gel concentration gradient made by the second method of making an electrophoresis medium in accordance with the present invention, the fractionation pattern was in the straight line form, and no disturbance arose in the fractionation pattern. On the other hand, with the gel membrane (4) having the gel concentration gradient made in Comparative Example 2 using the conventional technique, the fracionation pattern was in a large W-shaped undulation form, and disturbance arose therein.

The aforesaid results revealed that the electrophoresis medium membrane containing the aqueous polyacrylamide gel and having the concentration gradient and the constant membrane thickness prepared by the second method of making an electrophoresis medium in accordance with the present invention, wherein the two kinds of the aqueous solutions for gel formation having substantially equal viscosity values and different concentrations are mixed with each other, is of a high quality having a very constant membrane thickness and free of disturbance of fractionation patterns.

We claim:

1. A method of making an electrophoresis medium having a predetermined gradient in concentrations of an acrylamide compound and a cross-linking agent and containing a compound having at least one carbamoyl group in its molecule as a denaturing agent by mixing two kinds of aqueous solutions containing the acrylamide compound and the cross-linking agent in different concentrations such that a mixing ratio of the aqueous solutions to each other is changed gradually, thereby to form a predetermined gradual change in concentrations of the acrylamide compound and the cross-linking agent in the mixture, and carrying out cross-linking polymerization of the mixture in the presence of a polymerization initiator, wherein the improvement comprises the step of adjusting so that viscosity values of the two kinds of said aqueous solutions containing the acrylamide compound and the cross-linking agent in different concentrations prior to said mixing are substantially equal to each other.

2. A method as defined in claim 1 wherein a difference between the viscosity values of the two kinds of said aqueous solutions for gel formation is within the range of approximately 12% above and below a mean value of the viscosity values of the two kinds of the aqueous solutions for gel formation which are to be mixed with each other.

3. A method as defined in claim 1 wherein agarose is contained in at least one of said aqueous solutions for gel formation.

4. A method as defined in claim 1 wherein a water-soluble polymer is contained in at least one of said aqueous solutions for gel formation.

5. A method as defined in claim 1 wherein said denaturing agent is urea.

6. A method as defined in claim 1 wherein said electrophoresis medium is provided as a layer-shaped electrophoresis medium membrane between a planar support and a planar cover sheet.

7. A method as defined in claim 6 wherein said support and said cover sheet are sheet-shaped materials formed of polyethylene terephthalate.

8. A method as defined in claim 1, 2 or 3 wherein said electrophoresis medium is provided as a pillar-shaped electrophoresis medium inside of a tube-shaped support.

9. A method of making an electrophoresis medium having a predetermined gradient in concentrations of an acrylamide compound and a cross-linking agent by mixing two kinds of aqueous solutions containing the acrylamide compound and the cross-linking agent in different concentrations such that a mixing ratio of the aqueous solutions to each other is changed gradually, thereby to form a predetermined gradual change in concentrations of the acrylamide compound and the cross-linking agent in the mixture, and carrying out cross-linking polymerization of the mixture in the presence of a polymerization initiator, wherein the improvement comprises the step of adjusting so that viscosity values of the two kinds of said aqueous solutions containing the acrylamide compound and the cross-linking agent in different concentrations prior to said mixing are substantially equal to each other.

10. A method as defined in claim 9 wherein a difference between the viscosity values of the two kinds of said aqueous solutions for gel formation is within the range of approximately 12% above and below a mean value of the viscosity values of the two kinds of the aqueous solutions for gel formation which are to be mixed with each other.

11. A method as defined in claim 9 wherein a water-soluble polymer is contained in at least one of said aqueous solutions for gel formation.

12. A method as defined in claim 9 wherein an anionic surface active agent as a denaturing agent is contained in at least one of said aqueous solutions for gel formation.

13. A method as defined in claim 12 wherein said anionic surface active agent is an alkyl sulfate.

14. A method as defined in claim 13 wherein said alkyl sulfate is a sodium salt or a potassium salt of dodecylsulfuric acid.

15. A method as defined in claim 9 wherein said electrophoresis medium is provided as a layer-shaped electrophoresis medium membrane between a planar support and a planar cover sheet.

16. A method as defined in claim 15 wherein said support and said cover sheet are sheet-shaped materials formed of polyethylene terephthalate.

17. A method as defined in any of claims 9 to 14 wherein said electrophoresis medium is provided as a pillar-shaped electrophoresis medium inside of a tube-shaped support.

* * * * *